(12) United States Patent
Anderle et al.

(10) Patent No.: US 10,328,574 B2
(45) Date of Patent: Jun. 25, 2019

(54) ADJUSTMENT SYSTEM

(71) Applicant: Siemens Healthcare Diagnostics Products GmbH, Marburg (DE)

(72) Inventors: Klaus Anderle, Kronberg (DE); Matthias Korn, Nastaetten (DE)

(73) Assignee: Siemens Healthcare Diagnostics Products Gmbh, Marburg (DE)

( * ) Notice: Subject to any disclaimer, the term of this patent is extended or adjusted under 35 U.S.C. 154(b) by 336 days.

(21) Appl. No.: 15/411,871

(22) Filed: Jan. 20, 2017

(65) Prior Publication Data
US 2017/0210007 A1    Jul. 27, 2017

(30) Foreign Application Priority Data

Jan. 22, 2016 (EP) .................................. 16152386

(51) Int. Cl.
| | | |
|---|---|---|
| *G05B 19/18* | (2006.01) | |
| *B25J 9/16* | (2006.01) | |
| *B25J 13/08* | (2006.01) | |
| *G01N 35/10* | (2006.01) | |
| *G01N 35/00* | (2006.01) | |
| *G01N 35/04* | (2006.01) | |

(52) U.S. Cl.
CPC .......... *B25J 9/1633* (2013.01); *B25J 13/085* (2013.01); *G01N 35/0099* (2013.01); *G01N 35/04* (2013.01); *G01N 35/10* (2013.01); *G01N 35/1011* (2013.01); *G01N 2035/0494* (2013.01)

(58) Field of Classification Search
None
See application file for complete search history.

(56) References Cited

U.S. PATENT DOCUMENTS

| | | |
|---|---|---|
| 2011/0086432 A1 | 4/2011 | Herz et al. |
| 2012/0227471 A1 | 9/2012 | Smith et al. |
| 2014/0065017 A1 | 3/2014 | Herz et al. |
| 2015/0285831 A1 | 10/2015 | Kane |

FOREIGN PATENT DOCUMENTS

| | | |
|---|---|---|
| CN | 2718582 Y | 8/2005 |
| CN | 103988084 A | 8/2014 |

OTHER PUBLICATIONS

European Office Action and Search Report of European Application No. 16152386.5-1553 dated Jul. 14, 2016.
Chinese Search Report of Chinese Application No. 2016112356783 dated Dec. 21, 2017.

*Primary Examiner* — Bhavesh V Amin
(74) *Attorney, Agent, or Firm* — Dugan & Dugan, PC

(57) ABSTRACT

A method for adjusting a transfer apparatus fastened to a robotically displaceable transfer arm and comprising a holder for a liquid vessel in an automated analysis machine, by way of measuring a first and second force effect on the holder with the aid of a sensor, wherein, if the measured force effects do not deviate from one another by more than a predetermined amount, the transfer apparatus is sufficiently adjusted in respect of a receiving position, and wherein, if the measured force effects deviate from one another by more than a predetermined amount, an adjustment of the transfer apparatus in respect of the receiving position is carried out.

16 Claims, 2 Drawing Sheets

ADJUSTMENT SYSTEM

CROSS REFERENCE TO RELATED APPLICATION

This claims priority to European Patent Application No. EP 16152386.5, filed Jan. 22, 2016, which is hereby incorporated by reference herein in its entirety for all purposes.

FIELD

The invention lies in the field of automated in-vitro diagnostic systems. The subject matter of the invention relates to a method for adjusting an automatically operating analyzer for examining biological bodily fluids.

BACKGROUND

These days, a number of detection and analysis methods for determining physiological parameters in body fluid samples or other biological samples are performed in an automated manner and in large numbers in automatic analysis devices, also so-called in vitro diagnostic systems.

Current analysis devices are able to perform a multiplicity of detection reactions and analyses using a sample. In order to be able to perform a multiplicity of examinations in an automated manner, various apparatuses for the spatial transfer of measurement cells, reaction containers and reagent containers are required, such as, e.g., transfer arms with a gripper function, transport belts or rotatable transport wheels, and apparatuses for transferring liquids, such as, e.g., pipetting apparatuses. For samples, reagents, and also for the actual detection reaction, use is made of suitable vessels, which are also referred to as cuvettes. These usually comprise a closed wall and a possibly sealable opening for holding the respective liquid to be analyzed. The machines comprise a control unit which, by means of appropriate software, is able to largely independently plan and work through the work steps for the desired analyses.

Many of the analysis methods used in such analysis devices with automated operation are based on optical processes. These methods facilitate the qualitative and quantitative detection of analytes, i.e., the substances to be detected or to be determined in samples. The determination of clinically relevant parameters, such as, e.g., the concentration or activity of an analyte, is often implemented by virtue of part of a sample being mixed with one or more test reagents in a reaction vessel, which can also be the measurement cell, as a result of which, for example, a biochemical reaction or a specific binding reaction is initiated, bringing about a measurable change in an optical or other physical property of the test mix.

In current automatically operating analyzers, which are used for examining biological bodily fluids, the required reagents may be filled into a measurement cuvette by means of a pipetting apparatus with a pipetting needle. Here, with a cuvette gripper, the measurement cuvette is automatically displaced to different positions within the automated analysis machine by means of a robotic arm which is part of a robotic station. After the measurement, the used measurement cuvette is brought through a refuse chute in a refuse container for disposal purposes. A sensor may be provided on the cuvette gripper and/or on the robotic arm, with the aid of which force effects on the cuvette gripper or measurement cuvette may be measured.

When assembling an automatically operating analyzer, there always is a certain amount of uncertainty with respect to the positioning of, in particular, the robotic arms and other transfer and positioning systems. However, since these require exact positioning data for the automated procedure and exact cooperation, an exact adjustment is necessary. It may be carried out either manually with the aid of adjustment marks, highly precisely manufactured adjustment tools and/or automatically.

Usually, for the purposes of the automated adjustment, an appropriate sensor is initially present at the drive of the respective movable element of the transfer system to be adjusted, e.g., at a part of a transfer arm, said sensor forwarding information about the current position of the drive to the control unit. The transfer arm is then controlled by the control unit and moved toward a specific adjustment mark which, for example, is fixedly installed in the machine. Known adjustment systems often operate on a capacitive basis, with a needle, as a contact element, at the movable element being guided to a small metal surface at the adjustment mark. When contact is identified, the control unit stores the associated position of the drive. In other known adjustment systems, the contact element is arranged at the movable element by means of a hinge element, the hinge element having a self-restoring configuration, and a distance measuring sensor being assigned to a distance between the contact element and movable element.

Then, further assemblies in the machine, such as, e.g., receiving positions for liquid vessels, are arranged accordingly relative to the position of the adjustment mark. Ultimately, the transfer systems and the receiving positions must be adjusted correspondingly precisely relative to one another so that, e.g., liquid vessels may be transferred from a receiving position on one assembly to another receiving position on another assembly. In this case, attaching the adjustment mark and measuring the position of the adjustment mark relative to the position of, e.g., receiving positions may require much time and cost outlay and may be susceptible to errors. Furthermore, there may be changes in the relative position of the adjustment mark and the receiving positions during the operation of the machine, which may render a renewed, complicated adjustment and measurement of the machine necessary.

SUMMARY

It is therefore an object of the invention to provide an adjustment method, by means of which the time and cost outlay for adjustments may be reduced and which does not require any additional adjustment marks.

According to the invention, this object is achieved by the methods and articles described below.

It was discovered that an improved method for adjusting a transfer apparatus fastened to a robotically displaceable transfer arm and comprising a holder for a liquid vessel in an automated analysis machine, wherein the transfer apparatus may be moved with the aid of the transfer arm, may be achieved by means of the steps described below:

a) receiving a liquid vessel in the holder, b) measuring a first force effect on the holder with the received liquid vessel with the aid of a sensor, c) displacing the liquid vessel into a predetermined position at a predetermined level in a receiving position for the liquid vessel with the aid of the robotically displaceable transfer arm and measuring a second force effect on the holder with the received liquid vessel with the aid of the sensor, d) comparing the force effects measured in step b) and step c), wherein, if the force effects measured in step b) and step c) do not deviate from one another by more than a predetermined amount, the transfer apparatus is sufficiently adjusted in respect of the receiving position, and wherein, if the force effects measured in step b) and step c) deviate from one another by more than a predetermined amount, an adjustment of the transfer apparatus in respect of the receiving position is carried out.

This is advantageous in that, apart from the holder for the liquid vessel itself, no additional adjustment mark needs to be provided. This may lead to significant savings in terms of time and cost. Furthermore, this may lead to a significantly reduced susceptibility of the analyzer to errors. Furthermore, the adjustment state of the machine may be verified, e.g., permanently or at predetermined intervals by means of the method according to the invention during the running operation of the analyzer.

By way of example, a receiving position for a liquid vessel is a holder or a recess, which is able, in an interlocking manner, to surround and hold the liquid vessel at least in part, preferably the lower part thereof. Preferably, the receiving position comprises a wall which may interact with the liquid vessel. Preferably, the receiving position may be moved automatically by means of a robotic apparatus.

A suitable predetermined amount in respect of the deviation of the actions of the force is, e.g., greater than possible inaccuracies when measuring the actions of the force. Advantageously, where possible, the predetermined amount is selected to be only slightly greater than the inaccuracies when measuring the actions of the force. What can be achieved thereby is that the adjustment state may be ascertained in a comparatively accurate manner. However, if only a smaller accuracy in respect of ascertaining the adjustment state is sought after or if larger errors in the adjustment may be tolerated, the predetermined amount may optionally also be selected to be correspondingly larger. This may be advantageous in that the method may then be particularly robust and less susceptible to errors.

Possible inaccuracies when measuring the force effects may have very different causes. By way of example, they may occur as a consequence of imperfections in the structure and/or in the manufacturing process of the sensor. Furthermore, they may occur, for example, on account of changes in the influences from the surroundings. By way of example, such changes may relate to the temperature, external electromagnetic fields, vibrations and/or tremors. The inaccuracy of a measurement of the action of the force may, for example, be quantified by means of reference conditions under appropriate boundary conditions.

Furthermore, inaccuracies may occur due to statistical processes which, for example, may lead to corresponding noise. The inaccuracy of a measurement of the force effect on account of static processes may, for example, be quantified by multiple repetition of a measurement and statistical analysis of the measurement results.

In a preferred embodiment of the method for adjusting the transfer apparatus in respect of the receiving position, the method further comprises the following steps:

e) displacing the liquid vessel along a path in the receiving position into a modified position at the predetermined level in the receiving position with the aid of the transfer arm, the path extending at the predetermined level, and f) measuring a plurality of force effects on the holder with the received liquid vessel along the path with the aid of the sensor, g) ascertaining a correct position by evaluating the profile of the plurality of force effects along the path measured in step f).

This is advantageous in that there may immediately be an appropriate correction of the adjustment state if there is a significant deviation from a proper adjustment state. In particular, this is also possible during the running operation of the analyzer. A significant deviation from a proper adjustment state is present, for example, if the deviation is significant for the operation of the analyzer. By way of example, this may be the case if, on account of the deviation, there are errors and/or malfunctions during the operation of the analyzer or if the probability for the occurrence of such events assumes correspondingly elevated values.

In a further preferred embodiment of the method for adjusting the transfer apparatus in respect of the receiving position, the method further comprises the following steps:

h) displacing the liquid vessel into the corrected position at a predetermined level in the receiving position with the aid of the transfer arm, i) measuring a third force effect on the holder with the received liquid vessel with the aid of the sensor, j) comparing the force effects measured in step b) and step i), wherein, if the force effects measured in step b) and step i) do not deviate from one another by more than a predetermined amount, the transfer apparatus is sufficiently adjusted in respect of the receiving position, and wherein, if the force effects measured in step b) and step i) deviate from one another by more than a predetermined amount, a further adjustment of the transfer apparatus in respect of the receiving position is carried out by repeating steps e) to j).

This is advantageous in that checking of the adjustment state and a possibly required correction may be carried out iteratively.

In a further preferred embodiment, the path in step e) extends along one degree of freedom or along a plurality of different degrees of freedom.

In a further preferred embodiment, the method is performed in sequence for a plurality of different degrees of freedom.

In a further preferred embodiment of the method, the degree of freedom or the degrees of freedom are transversal or rotational degrees of freedom.

In a further preferred embodiment of the method, the method is performed in sequence for a plurality of receiving positions.

In a further preferred embodiment of the method, the sensor is arranged on the holder and/or the transfer arm.

In a further preferred embodiment of the method, there is a change in the position of the receiving position in step e) instead of the displacement of the liquid vessel with the aid of the transfer arm.

In a further preferred embodiment of the method, there is both a change in the position of the receiving position and a displacement of the liquid vessel with the aid of the transfer arm in step e).

Preferably, the change in the position of the receiving position is carried out by means of an automatically controlled robotic apparatus.

In a further preferred embodiment of the method, the sensor comprises a distance measuring sensor. A distance measuring sensor may capture a distance between two objects.

In a further preferred embodiment of the method, the distance measuring sensor comprises a Hall sensor and a magnet.

A Hall sensor (also referred to as Hall probe or Hall transducer, named after Edwin Hall) uses the Hall effect for measuring magnetic fields and flows or for capturing a position. In the case of the apparatus according to the invention, a magnet is embedded in the holder for the liquid vessel in a preferred embodiment, the magnetic field of which magnet is measured by a stationary Hall sensor. Since the field of the magnet at the location of the Hall sensor decreases with the distance of the Hall sensor from the magnet, the position of the magnet relative to the Hall sensor, and hence the distance of the holder for the liquid vessel relative to the Hall sensor, may be calculated from the value of the magnetic field at the location of the Hall sensor.

The transfer apparatus preferably comprises a flexible intermediate element.

Below, the term "flexible intermediate element" should denote a device attached between the holder and the robotically displaceable transfer arm, which device may be deformed in the case of force effects on the liquid vessel but, at the same time, is rigid enough such that the transfer arm and the holder are able to receive, transport and relinquish cuvettes.

Preferably, provision is made for the flexible intermediate element to consist of an elastic and/or damping material such as, for example—without being restricted thereto—elastomers, urethane rubber, caoutchouc, rubber, foam or spring steel. Moreover, a plurality of separate intermediate elements may also be used next to one another or above one another in order to ensure protection against twisting.

The flexible intermediate element ensures a certain deflectability of the holder in relation to the transfer arm when a force acts on the liquid vessel. At the same time, the flexible intermediate element however also restricts the deflection of the gripper when transporting the vessel, for example, by the thickness thereof and the elastic properties.

Below, the term "holder" should denote a device which is able to hold the liquid vessel. Preferably, the holder may also grip, hold and re-release the liquid vessel. What is advantageous here is if the holder comprises an integrally manufactured gripper for the liquid vessel. The holder is also referred to as cuvette holder.

In principle, gripping is a basic movement for picking up and holding, and establishes the connection between robot or analysis machine and workpiece, in this case a liquid vessel. Here, the type of synergy and the number of contact planes are decisive for a secure connection. The synergy can be obtained by forced, interlocking or adhesive pairings. When utilizing a forced pairing, the hold is generated by exercising pressure on the workpiece surface. In contrast to this, the hold is brought about in the interlocking pairing by enveloping the workpiece by an equal shape. Here, the transmitted clamping forces are very small during secure guiding. In the case of an adhesive pairing, the contact with the workpiece is brought about by utilizing adhesion.

Moreover, the gripper systems can be subdivided into mechanical, pneumatic, magnetic and adhesive systems according to their effect. These effects can also be utilized in combination in order to increase the flexibility of the gripper system.

Mechanical grippers are preferably used within the scope of this invention, but magnetic grippers in particular can also be used. There are one finger, two finger or multi-finger grippers as mechanical grippers with a rigid, rigid-hinged or elastic design.

The gripper preferred here is produced from a single piece. This allows reproducible production of an increased number of units since no individual parts have to be assembled and the proper operation of the assembled gripper only has to be checked randomly, but not for each individual unit.

The integral gripper is designed such that it can be deformed elastically and it is in a tensioned state. If it is moved against an obstruction with sufficient force, this results in a snap-effect and the gripper opens. Further movement in the direction of the obstruction causes the gripper to envelop the obstruction and said gripper snaps shut again due to the tensioned state as soon as the obstruction has been completely enveloped. Furthermore, the gripper only releases the enveloped obstruction when a release force is overcome, which force is necessary to reopen the gripper.

Thus, during the operation, the holder, for example, firstly moves in the direction of a liquid vessel as a result of sideways motion or to and fro motion of the transfer arm. This liquid vessel, which is preferably a cuvette, for example, stands in a receiving position. When it reaches the cuvette, the holder is pressed open by a cuvette flange and it envelops the cuvette in the case of further displacement due to the spring action of the plastic material or the tensioned state. After the cuvette has been surrounded, said cuvette can be lifted by means of an upward motion of the holder or the transfer arm. The cuvette is now being held and can be displaced by means of movement of the transfer arm.

In order to put down the cuvette in the holder, said cuvette is driven into a receiving position by movement of the transfer arm such that the cuvette remains in the receiving position if the holder is retracted, that is to say the holder is again pressed open, it releases the cuvette and it is then closed again in an elastic fashion.

Further subject matter of the invention relates to an automated analysis machine comprising at least one transfer apparatus which is fastened to a robotically displaceable transfer arm and comprises a holder for a liquid vessel, at least one sensor and at least one control machine, wherein the transfer apparatus may be moved with the aid of the transfer arm and wherein a force effect on the holder may be measured with the aid of the sensor, and wherein the control machine is configured in such a way that it may control the performance of a method for adjusting the transfer apparatus as claimed in one of the preceding claims.

In a preferred embodiment, the automated analysis machine comprises a multiplicity of receiving positions for a liquid vessel.

In a further preferred embodiment of the analysis machine, the adjustment system comprises a multiplicity of robotically displaceable transfer arms.

Further subject matter of the invention relates to the use of the method according to the invention in an automated analysis machine.

A "robotically displaceable transfer arm" is a transfer arm which is automatically displaceable by means of a drive. Thus, in particular, the transfer arm may carry out movements actively, e.g., driven by an electric motor or pneumatically.

By way of example, the transfer arm is part of a robotic station for treating, manipulating and analyzing chemical, clinical and/or biological samples. Here, the transfer arm serves, for example, to transport liquid vessels, such as, e.g., cuvettes, from a pipetting station to a photometer or a PCR cycler.

Preferably, the transfer arm is part of a laboratory robot or laboratory system, for example, for microbiology, analysis, forensics or clinical diagnostics.

Within the meaning of the invention, a "sample" should be understood to mean the material which presumably contains the substance to be detected (the analyte). In particular, the term "sample" comprises biological liquids of humans or animals, such as, e.g., blood, plasma, serum, sputum, exudates, bronchoalveolar lavage, lymph fluid, synovial fluid, semen, vaginal mucus, feces, urine, liquor, or else, e.g., tissue or cell culture samples prepared accordingly for photometric, preferably nephelometric determination by homogenization or cell lysis. Furthermore, plant liquids or tissues, forensic samples, water and sewage samples, foodstuff, pharmaceuticals may also serve as a sample which, possibly, should be subject to an appropriate sample pretreatment prior to the determination.

Quantitative detection involves measuring the amount, the concentration or the activity of the analyte in the sample. The expression "quantitative detection" also covers semi-quantitative methods, which can detect only the approximate amount, concentration or activity of the analyte in the sample or can serve only to provide a relative indication of amount, concentration or activity. Qualitative detection should be understood as the detection of the actual presence of the analyte in the sample, or the indication that the amount, concentration or activity of the analyte in the sample is below or above a defined threshold value or several defined threshold values.

By way of example, a measurement cuvette is a cuvette or reaction vessel made of glass, plastic or metal. Advantageously, the measurement cuvette is manufactured from optically transparent materials which may be advantageous, particularly when using optical analysis methods.

The terms "measurement cuvette" and "cuvette" are used synonymously.

BRIEF DESCRIPTION OF THE DRAWINGS

The invention is explained in more detail in an exemplary manner on the basis of the drawings. In the drawings.

The same parts have been provided with the same reference signs in all figures.

DETAILED DESCRIPTION

Figure 1:
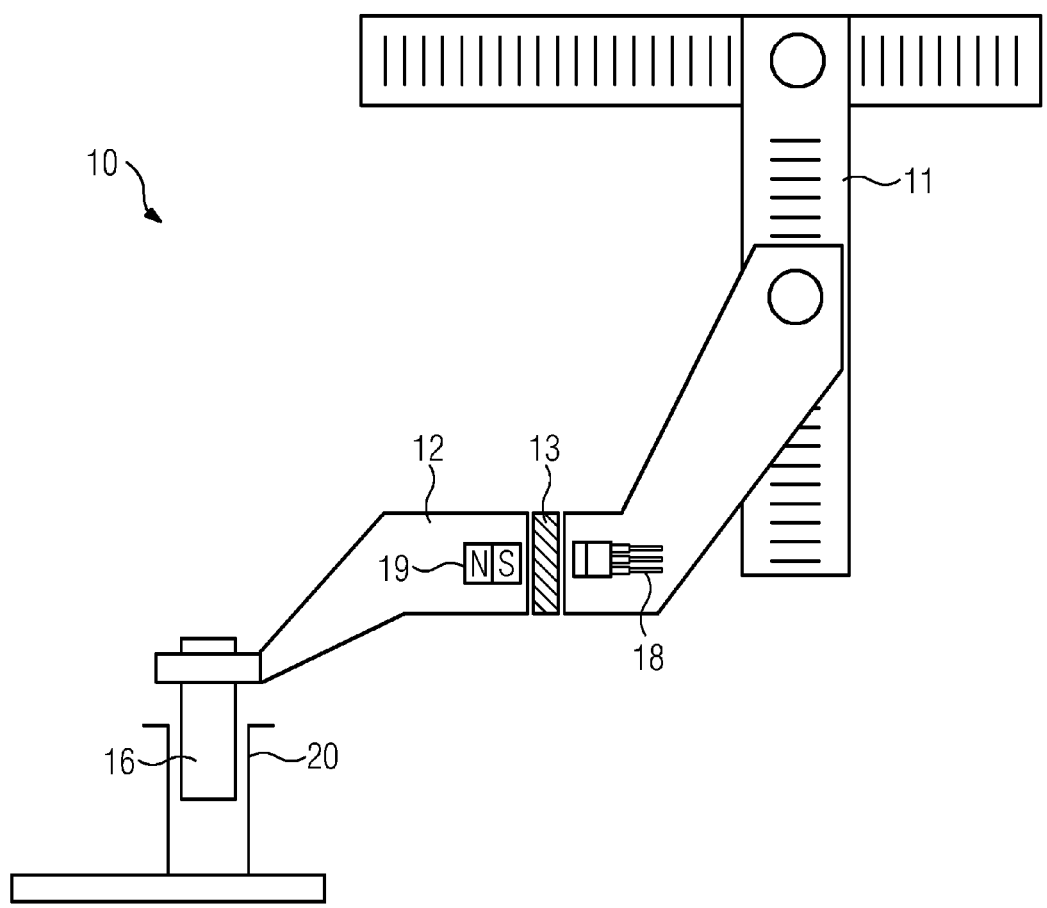
FIG. 1 schematically shows the design of a transfer apparatus (10) comprising a holder (12) for a liquid vessel (16), which holder may be moved with the aid of a robotically displaceable transfer arm (11), and FIG. 2 and FIG. 3 schematically show measured values of a measurement of a plurality of force effects on the holder with the received liquid vessel.

The transfer apparatus (10) in accordance with FIG. 1 is embedded into an analysis machine (not depicted in any more detail), which is configured to carry out a multiplicity of analyses of samples. To this end, the automated analysis machine comprises a multiplicity of transportation devices and pipetting devices (not shown) and furthermore a control unit for automated evaluation of the analyses.

The transfer apparatus (10) comprises a holder (12) for the liquid vessel (16), which holder may be moved with the aid of a robotically displaceable transfer arm (11). The liquid vessel (16) is situated at a predetermined level in a receiving position (20) for the liquid vessel (16).

Thus, the cuvette holder (12) and hence also the cuvette (16) may be displaced within the analysis machine by moving the transfer arm (11) in such an apparatus.

The apparatus further comprises a symbolically depicted Hall sensor (18), which is arranged on the transfer arm, captures the magnetic field emanating from a magnet arranged on the cuvette holder (12) and, in particular, is able to measure the movements thereof and forward these to a monitoring device (not depicted). This facilitates the measurement of force effects on the holder comprising the received liquid vessel with the aid of the sensor (18) by way of a relative movement between the sensor (18) and the cuvette holder (12).

Figure 2:
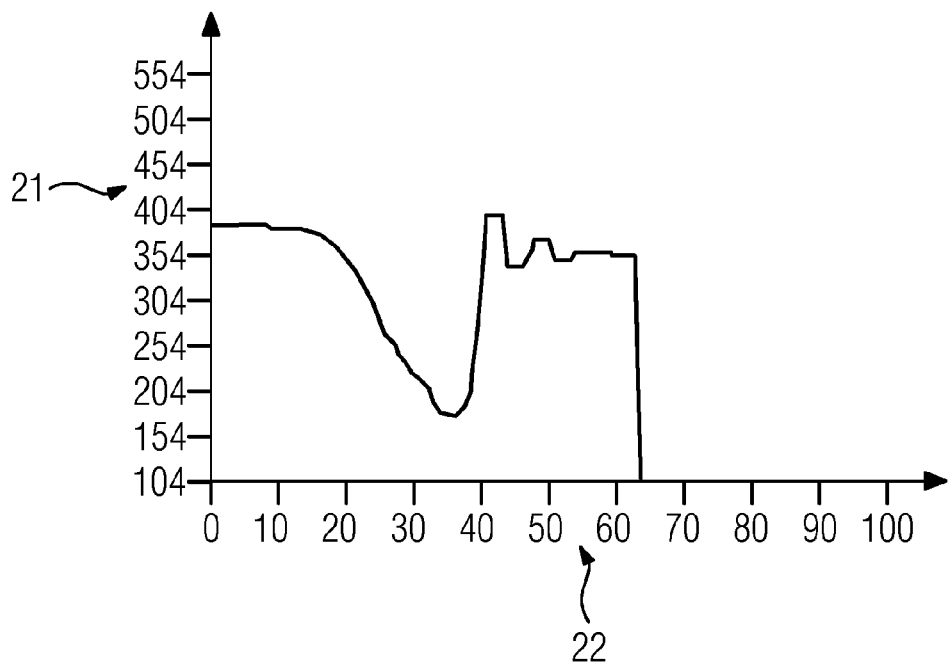

FIG. 2 schematically shows, with the aid of the sensor (18), measured values of a measurement of a plurality of force effects on the holder (12) comprising the received liquid vessel (16). What is plotted here is a measure for the force effect (21) against the position (22) of the holder.

The holder (12) is situated outside of the receiving position (20) in a range of the position (22) from approximately 40 to 62. On account of the interaction of the liquid vessel (16) and the holder (12) with the Earth's gravitational field, force effects in the region of approximately 354 are measured with the sensor (18) in this range of the position (22).

The holder (12) is situated within a receiving position (20) in a range from approximately 0 to 15 of the position (22). On account of the interaction of the liquid vessel (16) with a wall of the receiving position (20), force effects in the region of approximately 382 are measured with the sensor (18) in this range of the position (22). The increased force effect in the range 0 to 15 of the position (22) deviates by more than a predetermined measure from the force effect in the range of 40 to 62 of the position (22). Consequently, the transfer arm is not sufficiently adjusted in respect of the receiving position, and so there is an adjustment of the transfer arm in respect of the receiving position.

Figure 3:
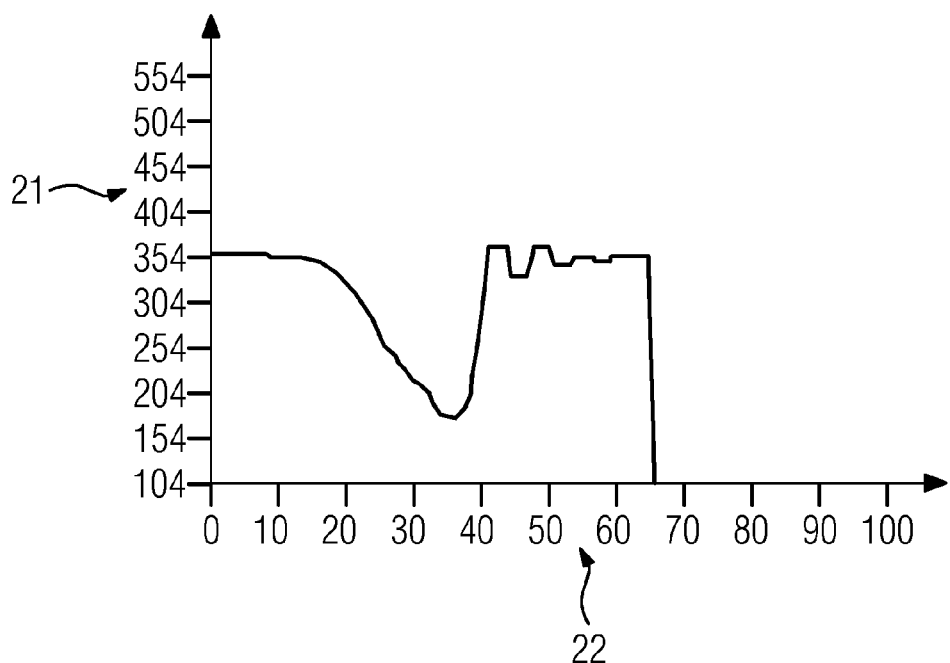

FIG. 3 schematically shows, with the aid of the sensor (18), measured values of a measurement of a plurality of force effects on the holder (12) comprising the received liquid vessel (16). What is plotted here is a measure for the force effect (21) against the position (22) of the holder.

The holder (12) is situated outside of the receiving position (20) in a range of the position (22) from approximately 40 to 62. On account of the interaction of the liquid vessel (16) and the holder (12) with the Earth's gravitational field, force effects in the region of approximately 354 are measured with the sensor (18) in this range of the position (22).

The holder (12) is situated within a receiving position (20) in a range from approximately 0 to 15 of the position (22). There is no significant interaction of the liquid vessel (16) with a wall of the receiving position (20) and force effects likewise in the region of approximately 354 are measured with the sensor (18) in this range of the position (22). The force effect in the range of 0 to 15 of the position (22) is therefore not elevated in relation to the force effect in the range of 40 to 62 of the position (22). Furthermore, the force effect in the range of 0 to 15 of the position (22) does not deviate by more than a predetermined measure from the force effect in the range of 40 to 62 of the position (22). Hence, the transfer arm is sufficiently adjusted in respect of the receiving position, and so there is no adjustment of the transfer arm in respect of the receiving position.

LIST OF REFERENCE SIGNS

10 Transfer apparatus
11 Robotically displaceable transfer arm

12 Holder
13 Flexible intermediate element
16 Liquid vessel
18 Sensor
19 Magnet
20 Receiving position
21 Force effect
22 Position

What is claimed is:

1. A method for adjusting a transfer apparatus fastened to a robotically displaceable transfer arm and comprising a holder for a liquid vessel in an automated analysis machine, wherein the transfer apparatus is configured to be moved with the aid of the transfer arm, comprising the following steps:
   (a) receiving a liquid vessel in the holder,
   (b) measuring a first force effect on the holder with the liquid vessel received in the holder with the aid of a sensor,
   (c) displacing the liquid vessel into a predetermined position at a predetermined level in a receiving position for the liquid vessel with the aid of the robotically displaceable transfer arm and measuring a second force effect on the holder with the liquid vessel received in the receiving position with the aid of the sensor, and
   (d) comparing the first and second force effects measured in step (b) and step (c),
   wherein, if the first and second force effects measured in step (b) and step (c) do not deviate from one another by more than a first predetermined amount, the transfer apparatus is sufficiently adjusted in respect of the receiving position, and
   wherein, if the first and second force effects measured in step (b) and step (c) deviate from one another by more than the first predetermined amount, an adjustment of the transfer apparatus in respect of the receiving position is carried out.

2. The method as claimed in claim 1, further comprising the following steps for adjusting the transfer apparatus in respect of the receiving position:
   (e) displacing the liquid vessel along a path in the receiving position into a modified position at the predetermined level in the receiving position with the aid of the transfer arm, the path extending at the predetermined level,
   (f) measuring a plurality of force effects on the holder with the liquid vessel received in the modified position along the path with the aid of the sensor, and
   (g) ascertaining a corrected position by evaluating a profile of the plurality of force effects along the path measured in step (f).

3. The method as claimed in claim 2, further comprising the following steps:
   (h) displacing the liquid vessel into the corrected position at the predetermined level in the receiving position with the aid of the transfer arm,
   (i) measuring a third force effect on the holder with the liquid vessel received in the corrected position with the aid of the sensor, and
   (j) comparing the first and third force effects measured in step (b) and step (i),
   wherein, if the first and third force effects measured in step (b) and step (i) do not deviate from one another by more than a second predetermined amount, the transfer apparatus is sufficiently adjusted in respect of the receiving position, and
   wherein, if the first and third force effects measured in step (b) and step (i) deviate from one another by more than the second predetermined amount, a further adjustment of the transfer apparatus in respect of the receiving position is carried out by repeating steps (e) to (j).

4. The method as claimed in claim 3, wherein the path in step (e) extends along one degree of freedom or a plurality of different degrees of freedom.

5. The method as claimed in claim 4, wherein the method is performed in sequence for the plurality of different degrees of freedom.

6. The method as claimed in claim 4, wherein the one degree of freedom or the plurality of different degrees of freedom are transversal or rotational degrees of freedom.

7. The method as claimed in claim 3, wherein the method is performed in sequence for a plurality of receiving positions.

8. The method as claimed in claim 3, wherein the first predetermined amount and the second predetermined amount are the same.

9. The method as claimed in claim 2, further comprising changing the modified position of the receiving position in step (e) instead of the displacing the liquid vessel with the aid of the transfer arm.

10. The method as claimed in claim 2, wherein step (e) also comprises changing the modified position of the receiving position.

11. The method as claimed in claim 1, wherein the sensor is arranged on the holder or the transfer arm.

12. The method as claimed in claim 1, wherein the sensor comprises a distance measuring sensor.

13. The method as claimed in claim 12, wherein the distance measuring sensor comprises a Hall sensor and a magnet.

14. An automated analysis machine comprising at least one transfer apparatus which is fastened to a robotically displaceable transfer arm and comprises a holder for a liquid vessel, at least one sensor and at least one control machine, wherein the transfer apparatus is configured to be moved with the aid of the transfer arm and wherein a force effect on the holder is capable of being measured with the aid of the sensor,
   wherein the control machine is configured to perform the method as claimed in claim 1.

15. The automated analysis machine as claimed in claim 14, wherein the automated analysis machine comprises a multiplicity of receiving positions for a liquid vessel.

16. The automated analysis machine as claimed in claim 14, further comprising a multiplicity of robotically displaceable transfer arms.

* * * * *